United States Patent
Manak

(10) Patent No.: US 7,949,174 B2
(45) Date of Patent: May 24, 2011

(54) SYSTEM AND METHOD FOR CALIBRATING AN X-RAY DETECTOR

(75) Inventor: Joseph J. Manak, Albany, NY (US)

(73) Assignee: General Electric Company, Niskayuna, NY (US)

( * ) Notice: Subject to any disclaimer, the term of this patent is extended or adjusted under 35 U.S.C. 154(b) by 1218 days.

(21) Appl. No.: 11/583,669

(22) Filed: Oct. 19, 2006

(65) Prior Publication Data

US 2008/0093545 A1    Apr. 24, 2008

(51) Int. Cl.
*G06K 9/00* (2006.01)

(52) U.S. Cl. ........ 382/132; 382/100; 382/128; 382/131; 382/254; 382/280; 250/252.1; 378/207

(58) Field of Classification Search ............ 382/100, 382/128, 131, 132, 280; 250/252.1; 378/207
See application file for complete search history.

(56) References Cited

U.S. PATENT DOCUMENTS

| | | | | |
|---|---|---|---|---|
| 6,651,018 | B2 * | 11/2003 | Kropfeld et al. | 702/85 |
| 6,879,660 | B2 * | 4/2005 | Dhawale et al. | 378/98.8 |
| 6,890,098 | B2 * | 5/2005 | Rosner et al. | 378/196 |
| 6,980,624 | B2 * | 12/2005 | Li et al. | 378/23 |
| 2003/0133601 | A1 * | 7/2003 | Giger et al. | 382/128 |
| 2005/0061963 | A1 * | 3/2005 | Spahn et al. | 250/252.1 |
| 2006/0262147 | A1 * | 11/2006 | Kimpe et al. | 345/690 |

* cited by examiner

*Primary Examiner* — Matthew C Bella
*Assistant Examiner* — Eric Rush
(74) *Attorney, Agent, or Firm* — Fletcher Yoder

(57) ABSTRACT

A method and system are provided for generating high and low-frequency components for the pixels of a detector array. The method includes the act of generating a gain map image comprised of gain coefficients for one or more pixels of a detector array. A frequency-based transform is applied to the gain map image to generate a high-frequency component and a low-frequency component of the gain map coefficients for each pixel. The high and low-frequency components may be differentially applied in the processing of images.

17 Claims, 2 Drawing Sheets

SYSTEM AND METHOD FOR CALIBRATING AN X-RAY DETECTOR

STATEMENT REGARDING FEDERALLY SPONSORED RESEARCH & DEVELOPMENT

Figure 1:
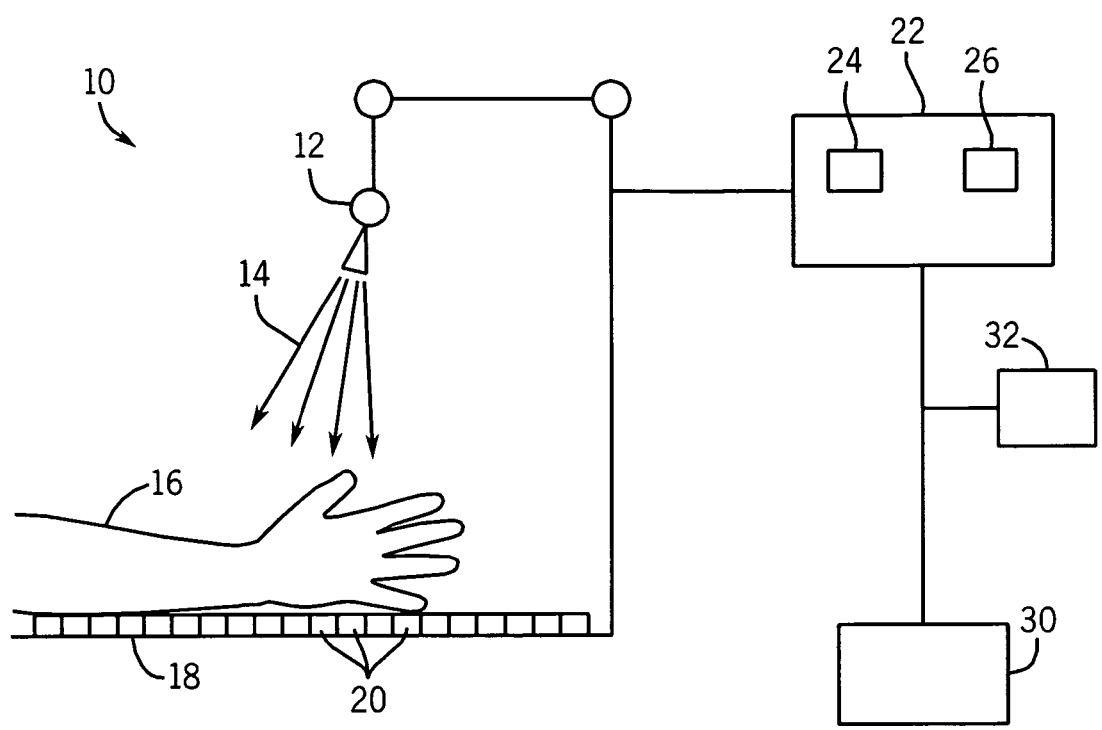

This invention was made with Government support under contract number DAMD 17-00-2-0009 awarded by the Department of Defense. The Government has certain rights in the invention.

BACKGROUND

The invention relates generally to imaging techniques and, more specifically, to the calibration of an X-ray detector.

Non-invasive imaging broadly encompasses techniques for generating images of the internal structures or regions of an object or person that are otherwise inaccessible for visual inspection. One of the best known uses of non-invasive imaging is in the medical arts where these techniques are used to generate images of organs and/or bones inside a patient which would otherwise not be visible. Examples of such non-invasive imaging modalities include X-ray radiography and other X-ray based imaging techniques, such as tomosynthesis.

For example a medical X-ray radiography system typically operates by projecting X-rays from an X-ray source through an imaging volume. A portion of the X-rays pass through, and are attenuated by, a portion of a patient, such as the chest or an arm or leg. The attenuated X-rays are detected by an array of detector elements that produce signals representing the attenuation of the incident X-rays. The signals are processed and reconstructed to form images of the imaged region.

For example, a digital detector may be comprised of an array of individual photodetectors disposed beneath a single, monolithic scintillator or individual scintillators. The scintillators typically generate optical light when impacted by X-rays. The photodetectors, in turn, detect the optical light and generate responsive electrical signals that can be read out and, based on the location of the photodetector on the panel, used to generate an image. In such systems, the degree of output signal generated by a photodetector in response to a given X-ray input is known as the gain of the photodetector.

Photodetectors, however, may vary in their ability to detect the optical light and/or in their ability to generate a responsive output signal. As a result, not all of the photodetectors of the detector array may generate an equivalent output signal in response to the same X-ray dose, i.e., individual photodetectors may have different, intrinsic gain functions. In systems where the X-ray source and the detector have a fixed geometry, i.e., the source and detector do not move relative to one another, calibration addresses these differences in gain by providing a correaction factor for each photodiode so that, in response to a known X-ray exposure, the gain differences between photodetectors can be compensated. For example, the array of photodetectors may be exposed to a uniform field of X-rays and corrections factors determined for each photodetector so that, after application of the respective correaction factor, each photodiode produces a uniform signal. In this manner, each photodetector can be corrected to generate a uniform signal in the presence of such a uniform field.

Calibration, however, is less effective in systems where the X-ray source and detector are not fixed relative to one another. In particular, in such systems, output differences between photodetectors may be the result not only of differences attributable to the photodetectors themselves but also the result of the relative geometry of the X-ray source and the detector during an exposure event. Therefore, a correaction factor derived at one source/detector geometry may not properly correct for photodetector output differences at other source/detector geometries. In such systems, it would be desirable to distinguish between the portion of the differences in photodetector outputs attributable to source/detector geometry and the portions attributable to the photodetectors themselves.

BRIEF DESCRIPTION

A method for generating image correaction factors is provided. The method includes the act of generating a gain map image comprised of gain correaction coefficients for one or more pixels of a detector array. A frequency-based transform is applied to the gain map image to generate a high-frequency component of the gain map coefficients and a low-frequency component of the gain map coefficients for each pixel. Corresponding claims to tangible, machine readable media comprising code executable to perform these acts are also provided.

A method is provided for processing an image. The method includes the act of acquiring an image using an imaging system comprising a source and a detector array. One or more low-frequency components determined for pixels of the detector array are adjusted to account for the location of the source relative to the detector array during acquisition of the image. The image is corrected using the one or more adjusted low-frequency components. Corresponding claims to tangible, machine readable media comprising code executable to perform these acts are also provided.

An imaging system is provided. The imaging system includes a detector array comprising a plurality of detector elements and a source configured to emit radiation toward the detector array. The source is movable relative to the detector array. The imaging system also includes a system controller configured to control operation of at least one of the detector array or the source and an image processing component. The image processing component is configured to process signals generated by the detector array in response to the emitted radiation to generate an image. In addition, the image processing component is configured to adjust one or more low-frequency components determined for pixels of the detector array to account for the location of the source relative to the detector array during acquisition of the image and to correct the image using the one or more adjusted low-frequency components.

DRAWINGS

Figure 2:
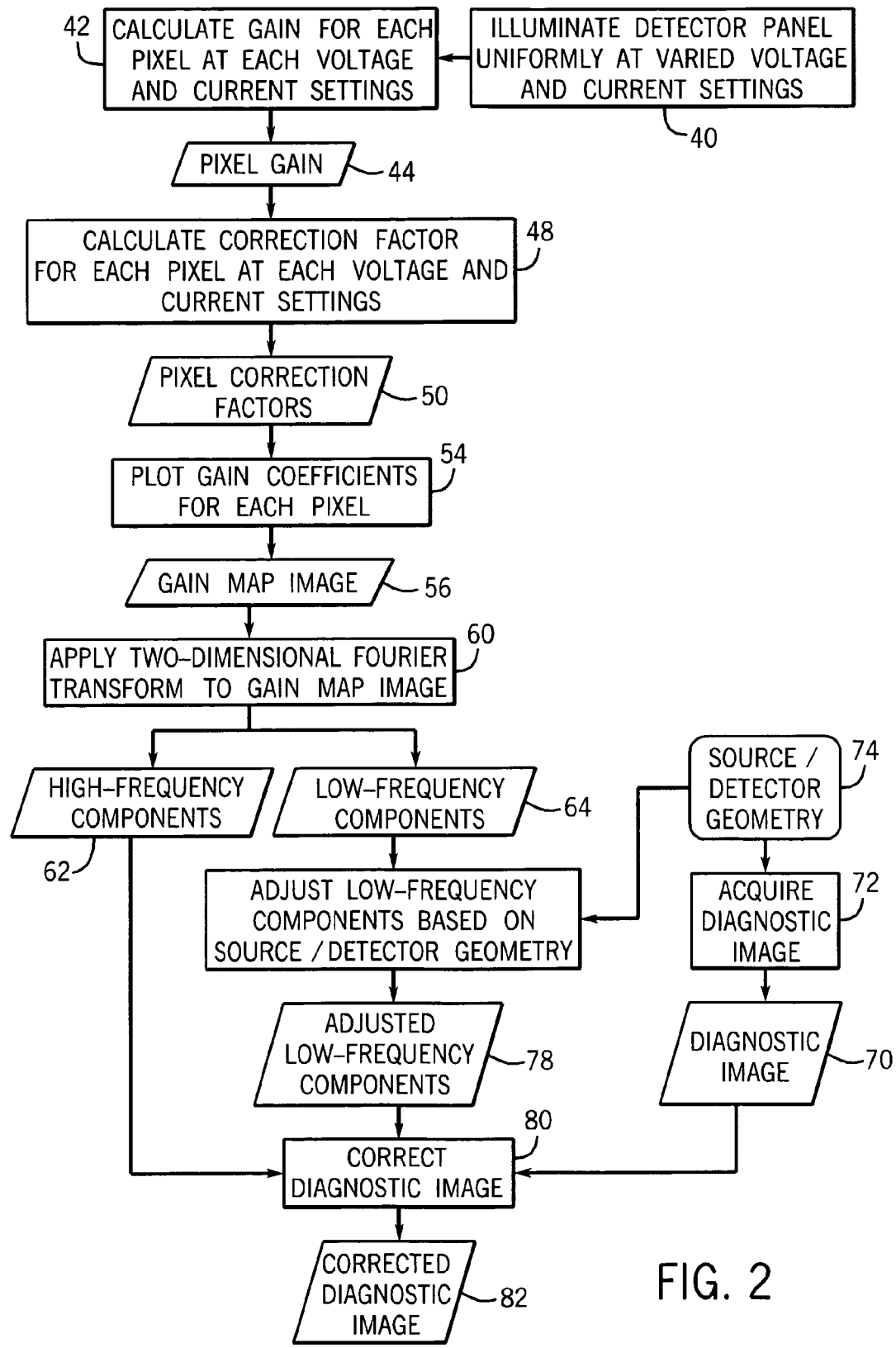

These and other features, aspects, and advantages of the present invention will become better understood when the following detailed description is read with reference to the accompanying drawings in which like characters represent like parts throughout the drawings, wherein:

FIG. 1 is a diagrammatical view of an exemplary imaging system in the form of a radiographic X-ray imaging system for use in producing images in accordance with aspects of the present technique; and FIG. 2 is a flowchart depicting exemplary actions for processing images acquired using the system of FIG. 1, in accordance with aspects of the present technique.

DETAILED DESCRIPTION

FIG. 1 illustrates diagrammatically an imaging system 10 for acquiring and processing projection data to generate radiographic images in accordance with the present technique. In the illustrated embodiment, system 10 is a mobile X-ray imaging system designed both to acquire original image data, and to process the image data for display and analysis in accordance with the present technique. In other embodiments, the system 10 is a tomosynthesis system or other system in which images are acquired over a limited number of view angles. The system 10 comprises an X-ray source 12 configured to emit X-rays 14. In one exemplary embodiment the X-ray source 12 is an X-ray tube with a rotating anode and thermionic electron source. In other embodiments the X-ray source 12 may be a stationary anode X-ray tube with a solid-state or thermionic electron source, or may be other sources of X-ray radiation suitable for the acquisition of medical images.

The X-rays 14 pass through a region in which an object, such as the arm 16 of a patient, is positioned. A portion of the X-ray radiation 14 passes through or around the object and impacts a detector array 18. Detector elements 20, i.e., pixels, of the array 18 produce electrical signals that represent the intensity of the incident X-rays 14. These signals are acquired and processed to generate images of the features within the object, such as arm 16 in the depicted example. In one embodiment the detector array 18 comprises a flat panel detector, such as a monolithic type detector array consisting of a large and/or continuous scintillation surface overlaying a photodetection assembly, such as an array of photodiodes.

Source 12 is controlled by a system controller 22, which furnishes both power, and control signals for radiographic examinations. In the depicted embodiment, the system controller 22 controls the source 12 via an X-ray controller 24, which may be a component of the system controller 22. In such an embodiment, the X-ray controller 24 may be configured to provide power and timing signals to the X-ray source 12 and/or to otherwise control the activation and operation of the X-ray source 12.

Moreover, the detector 18 is coupled to the system controller 22, which commands acquisition of the signals generated in the detector 18. In the depicted embodiment, the system controller 22 acquires the signals generated by the detector 18 using a data acquisition system 26. The data acquisition system 26 receives data collected by readout electronics of the detector 18. In one embodiment, the data acquisition system 26 receives sampled analog signals from the detector 18 and converts the data to digital signals for subsequent processing by an image processing component 30. In alternative embodiments, the readout circuitry of the detector 18 converts the signals to a digital form prior to providing the signals to the data acquisition system 26. The data acquisition system 26 may execute various signal processing and filtration functions with regard to the acquired image signals, such as for initial adjustment of dynamic ranges, interleaving of digital image data, and so forth.

In general, system controller 22 commands operation of the imaging system 10 (such as via the operation of the source 12 and detector 18) to execute examination protocols and to process acquired data. In the present context, system controller 24 also includes signal processing circuitry, typically based upon a general purpose or application-specific digital computer, associated memory circuitry for storing programs and routines executed by the computer (such as routines for executing image processing and reconstruction techniques described herein), as well as configuration parameters and image data, interface circuits, and so forth.

In the depicted embodiment, the image signals acquired and processed by the system controller 24 are provided to the image processing component 30 for generation of images. The processing component 30 may consist of or include one or more conventional microprocessors or special purpose processors, such as graphics coprocessors. The data collected by the data acquisition system 26 may be transmitted to the processing component 30 directly or after storage in a memory. It should be understood that any type of memory suitable to store a large amount of data might be utilized by such an exemplary system 10. Moreover, the memory may be located at the acquisition system site or may include remote components for storing data, processing parameters, and routines for image processing and reconstruction.

The processing component 30 is configured to receive commands from and to output images to an operator via an operator workstation 32 typically equipped with a keyboard and other input devices. An operator may control the system 10 via the input devices. Thus, the operator may observe the acquired images and/or otherwise operate the system 10 via the operator workstation 40. For example, a display on the operator workstation 32 may be utilized to observe the generated images and to control imaging. Additionally, the images may also be printed to a printer that may be a component of or coupled to the operator workstation 32.

Further, the processing component 30 and operator workstation 32 may be coupled to other output devices, which may include standard or special purpose computer monitors and associated processing circuitry. One or more operator workstations 32 may be further linked to the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

It should be further noted that the operator workstation 32 may also be coupled to a picture archiving and communications system (PACS). Such a PACS might be coupled to a remote client, radiology department information system (RIS), hospital information system (HIS) or to an internal or external network, so that others at different locations may gain access to the image, the image data, and optionally the variance data.

While the preceding discussion has treated the various exemplary components of the imaging system 10 separately, one of ordinary skill in the art will appreciate that some or all of these various components may be provided within a common platform or in interconnected platforms. For example, the processing component 30, memory, and operator workstation 32 may be provided collectively as a general or special purpose computer or workstation configured to operate in accordance with the present technique. Likewise, the system controller 22 may be provided as part of such a computer or workstation.

In one embodiment of the present technique, the system 10 of FIG. 1 is calibrated and the calibrated system used to acquire radiographic data and generate useful medical images. For example, referring to FIG. 2, exemplary acts for calibrating and using the system 10 of FIG. 1 are depicted. In this embodiment, the detector panel 18 is illuminated uniformly (Block 40) by the X-ray source 12 at various voltage and current settings of the X-ray source 12. The resulting flat-field images are used to calculate (Block 42) the gain 44 of each pixel 20 at each of the current and voltage settings used to generate the X-rays 14 in the illumination step of Block 40. The pixel gain values 44 are then used to calculate (Block 48) correaction factors 50 for each pixel 20 for each of the respective voltage and current settings of the X-ray source 12.

In the depicted embodiment, the pixel gains 44 and correaction factors 50 are used to derive corresponding slope and offset values for the gain functions associated with each respective detector pixel 20. For example, in instances where the gain functions are linear, the slope and offset calculation may simply correspond to the calculating the line representing the gain function. In instances where the gain functions are non-linear, the gain function may include a quadratic term. Each of the calculated gain coefficients are plotted (Block 54) for each pixel 20, forming a two-dimensional gain map image 56. For example, the gain map image 56 may be a two-dimensional representation of each coefficient value depicted at the corresponding pixel spatial location.

A two-dimensional Fourier transform, or other suitable frequency based transform, is applied (Block 60) to the gain map image 56, yielding high-frequency components 62 and low-frequency components 64 of the gain function coefficients for each pixel 20. For example, in one embodiment the high and low-frequency components 62, 64 are generated by a function which weights the two-dimensional Fast Fourier Transform image to generate high-frequency components 62 and uses the inverse of the function to generate the low-frequency components 64. In particular, in one embodiment the suitability of this approach is evidenced by the bi-modal distribution seen in the Fourier transform. As will be appreciated by those of ordinary skill in the art, each mode or hump of the distribution can be appropriately designated as including the respective high or low-frequency components 62, 64, which can be separated by use of the suitable function and inverse function as described above.

The high-frequency components 62 are generally believed to correspond to electrical or other response differences intrinsic to the respective pixels 20 of the detector array 18, for example due to scintillator and/or photodiode variability. Therefore, the high-frequency components 62 are believed to be independent of the location of the X-ray source 12. Conversely, the low-frequency components 64 are generally believed to be, partially or entirely, geometry dependent due to the general inability to generate a uniform field from the X-ray source 12 on the detector array 18 in clinical operation. For example, the position of the X-ray source 12 during image acquisition results in differences in distance between the X-ray source 12 and different pixels 20 of the detector array 18, leading to response differences attributable to the source/detector geometry when the X-ray source 12 and detector array 18 can be moved relative to one another. In addition, rotating anode X-ray tubes have a "heel" effect due to the geometry of the X-ray target that can result in the presence of such low frequency components 64. Therefore, as will be appreciated by those of ordinary skill in the art, for each pixel 20 a high-frequency gain component 62 attributable to the pixel itself is calculated along with a low-frequency gain component 64 generally attributable to the location of the X-ray source 12. To determine the appropriate function to separate the low frequency component 64 from the high frequency position independent component 62 one can obtain a series of flat field images from various source locations. Using this data one can then separate the position independent high frequency component 62 from the position dependent low frequency component 64 as described above.

In view of the respective high-frequency components 62 and low-frequency components 64 derived for a detector 18 of an imaging system 10, images acquired by the system 10 may be suitably processed to correct for gain variations between the respective pixels 20. For example, in the depicted embodiment, a diagnostic image 70 is acquired (Block 72) by the system 10. The acquisition of the image 70 is associated with a corresponding source/detector geometry 74 that describes the relative positions of the source 12 and detector array 18 to one another at the time of image acquisition. Based on this source/detector geometry 74, the low-frequency components 64 determined for the detector array 18 are adjusted (Block 76) to account for the geometry 74. In the depicted embodiment, the adjusted low-frequency components 78 and the high-frequency components 62 (which are not adjusted based on source/detector geometry 74 but may be adjusted based on other factors) are used to correct (Block 80) the diagnostic image 70 to generate a gain corrected diagnostic image 82. The gain corrected diagnostic image 82 may then be printed and/or displayed at the operator workstation 32 of FIG. 1 for review by a technologist.

While only certain features of the invention have been illustrated and described herein, many modifications and changes will occur to those skilled in the art. For example, though the present discussion has been in the context of medical imaging using radiographic systems, one of ordinary skill in the art will appreciate that the present techniques are equally applicable to tomosynthesis systems and also to non-medical imaging applications employing X-ray sources that may move relative to the detection apparatus. For example, the present techniques may also be applied to non-invasive and/or non-destructive imaging techniques used for security and quality control applications in the fields of baggage and package screening, manufacturing quality control, security screening and so forth. It is, therefore, to be understood that the appended claims are intended to cover all such modifications and changes as fall within the true spirit of the invention.

The invention claimed is:

1. A method for generating image correction factors, comprising:
    accessing a gain map image comprised of gain correction coefficients for one or more pixels of a detector array;
    applying a frequency-based transform to the gain map image to generate a high-frequency component of the gain map coefficients and a low-frequency component of the gain map coefficients for each pixel;
    determining the appropriate low-frequency components based on a source/detector geometry associated with an imaging system during the acquisition of an image;
    adjusting the low-frequency components based on the source-detector geometry; and
    correcting the image using the adjusted low-frequency components and the unadjusted high-frequency components.

2. The method of claim 1, wherein the frequency-based transform comprises a two-dimensional Fourier transform.

3. A method for processing an image, comprising:
    acquiring an image using an imaging system comprising a source and a detector array;
    adjusting one or more low-frequency components of respective gain coefficients determined for pixels of the detector array based on the location of the source relative to the detector array during acquisition of the image; and
    correcting the image using the one or more adjusted low-frequency components and one or more unadjusted high-frequency components of the respective gain coefficients.

4. The method of claim 3, wherein the one or more low-frequency components are derived by applying a two-dimensional Fourier transform to a gain map image associated with the detector.

5. The method of claim 3, wherein the imaging system comprises one of a radiographic X-ray imaging system or a tomosynthesis imaging system.

6. The method of claim 3, wherein the imaging system comprises one of a medical imaging system, a non-destructive testing system, or a screening system suitable for imaging baggage or packages.

7. The method of claim 3, wherein the source comprises a movable X-ray tube.

8. The method of claim 3, wherein the detector array comprises a flat-panel detector.

9. One or more tangible, machine readable media, comprising code executable to perform the acts of:
   accessing a gain map image comprised of gain correction coefficients for one or more pixels of a detector array;
   applying a frequency-based transform to the gain map image to generate a high-frequency component of the gain map coefficients and a low-frequency component of the gain map coefficients for each pixel;
   determining the appropriate low-frequency components based on a source/detector geometry associated with an imaging system during the acquisition of an image;
   adjusting the low-frequency components based on the source-detector geometry; and
   correcting the image using the adjusted low-frequency components and the unadjusted high-frequency components.

10. The one or more tangible, machine readable media of claim 9, wherein the frequency-based transform comprises a two-dimensional Fourier transform.

11. One or more tangible, machine readable media, comprising code executable to perform the acts of:
   acquiring an image using an imaging system comprising a source and a detector array;
   adjusting one or more low-frequency components of respective gain coefficients determined for pixels of the detector array based on the location of the source relative to the detector array during acquisition of the image; and
   correcting the image using the one or more adjusted low-frequency components and one or more unadjusted high-frequency components of the respective gain coefficients.

12. An imaging system, comprising:
   a detector array comprising a plurality of detector elements;
   a source configured to emit radiation toward the detector array, wherein the source is movable relative to the detector array;
   a system controller configured to control operation of at least one of the detector array or the source;
   an image processing component configured to process signals generated by the detector array in response to the emitted radiation to generate an image, wherein the image processing component is configured to adjust one or more low-frequency components of respective gain coefficients determined for pixels of the detector array based on the location of the source relative to the detector array during acquisition of the image and to correct the image using the one or more adjusted low-frequency components and one or more unadjusted high-frequency components of the respective gain coefficients.

13. The imaging system of claim 12, wherein the detector array comprises a flat-panel detector.

14. The imaging system of claim 12, wherein the source comprises a movable X-ray tube.

15. The imaging system of claim 12, wherein the imaging system comprises one of a medical imaging system, a non-destructive testing system, or a screening system suitable for imaging baggage or packages.

16. The imaging system of claim 12, wherein the imaging system comprises one of a radiographic X-ray imaging system or a tomosynthesis imaging system.

17. The imaging system of claim 12, wherein the one or more low-frequency components are derived by applying a two-dimensional Fourier transform to a gain map image associated with the detector.

* * * * *

UNITED STATES PATENT AND TRADEMARK OFFICE
CERTIFICATE OF CORRECTION

| | | |
|---|---|---|
| PATENT NO. | : 7,949,174 B2 | Page 1 of 1 |
| APPLICATION NO. | : 11/583669 | |
| DATED | : May 24, 2011 | |
| INVENTOR(S) | : Manak | |

It is certified that error appears in the above-identified patent and that said Letters Patent is hereby corrected as shown below:

In Column 1, Line 52, delete "correaction" and insert -- correction --, therefor.

In Column 1, Line 57, delete "correaction" and insert -- correction --, therefor.

In Column 1, Line 67, delete "correaction" and insert -- correction --, therefor.

In Column 2, Line 11, delete "correaction" and insert -- correction --, therefor.

In Column 2, Line 13, delete "correaction" and insert -- correction --, therefor.

In Column 5, Line 1, delete "correaction" and insert -- correction --, therefor.

In Column 5, Lines 4-5, delete "correaction" and insert -- correction --, therefor.

Signed and Sealed this
Twelfth Day of July, 2011

David J. Kappos
*Director of the United States Patent and Trademark Office*